(12) United States Patent
Fitzpatrick et al.

(10) Patent No.: US 10,660,761 B2
(45) Date of Patent: May 26, 2020

(54) TOTAL KNEE REPLACEMENT PROSTHESIS ASSEMBLY

(71) Applicant: FITZBIONICS LIMITED, Surrey (GB)

(72) Inventors: Noel Fitzpatrick, Surrey (GB); Jayantilal Meswania, Surrey (GB)

(73) Assignee: FITZBIONICS LIMITED, Surrey (GB)

( * ) Notice: Subject to any disclaimer, the term of this patent is extended or adjusted under 35 U.S.C. 154(b) by 77 days.

(21) Appl. No.: 15/746,201

(22) PCT Filed: Jul. 20, 2016

(86) PCT No.: PCT/GB2016/052197
§ 371 (c)(1),
(2) Date: Jan. 19, 2018

(87) PCT Pub. No.: WO2017/013428
PCT Pub. Date: Jan. 26, 2017

(65) Prior Publication Data
US 2018/0206998 A1    Jul. 26, 2018

(30) Foreign Application Priority Data

Jul. 20, 2015 (GB) .................................. 1512696.4

(51) Int. Cl.
*A61F 2/38*        (2006.01)
*A61F 2/30*        (2006.01)

(52) U.S. Cl.
CPC ............ *A61F 2/3845* (2013.01); *A61F 2/384* (2013.01); *A61F 2/385* (2013.01); *A61F 2/389* (2013.01);
(Continued)

(58) Field of Classification Search
CPC ...... A61F 2/3804; A61F 2/3836; A61F 2/384; A61F 2/385; A61F 2/3845; A61F 2/3854; A61F 2002/30624
See application file for complete search history.

(56) References Cited

U.S. PATENT DOCUMENTS 5,282,867 A * 2/1994 Mikhail ................ A61F 2/0811
                                                    623/13.12
5,370,701 A   12/1994 Finn
(Continued)

FOREIGN PATENT DOCUMENTS

EP    0420460    4/1991
EP    0812582    12/1997
(Continued)

OTHER PUBLICATIONS

Great Britain Search Report in priority application GB1512696.4 dated Apr. 7, 2016.
International Search Report and Written Opinion in parent PCT application PCT/GB2016/052197 dated Sep. 30, 2016.

*Primary Examiner* — Megan Y Wolf
(74) *Attorney, Agent, or Firm* — Andrus Intellectual Property Law

(57) ABSTRACT

A total knee replacement prosthesis assembly (10) comprising a femoral component (20), a tibial component (30) having a tibial platform (32), and a bearing component (40), the bearing component having an inferior side (40b) and a superior side (40a), the bearing component being adapted to be arranged between the femoral component and tibial platform when assembled, the tibial platform having a post (36) upstanding from it and the bearing component having a post recess (46) in its inferior side for receiving the post, the bearing component being rotatable about the post when assembled, the post and bearing component each having a transverse bore and the assembly further comprising an axle (60), at least part of the axle being received through the (Continued)

transverse bore (38) in the post when assembled and at least part of the axle being received through the transverse bore (52) in the bearing component when assembled, the axle being configured to provide an axis of rotation between the femoral component and bearing component which is fixed relative to the femoral component and the bearing component in use.

19 Claims, 3 Drawing Sheets

(52) U.S. Cl.
CPC ...... *A61F 2/3859* (2013.01); *A61F 2002/307* (2013.01); *A61F 2002/30364* (2013.01); *A61F 2002/30369* (2013.01)

(56) References Cited

U.S. PATENT DOCUMENTS

| | | | | |
|---|---|---|---|---|
| 5,458,644 | A | * 10/1995 | Grundei | ............... A61F 2/3845 623/20.24 |
| 2005/0107886 | A1 | * 5/2005 | Crabtree | ................ A61F 2/385 623/20.24 |
| 2014/0277535 | A1 | 9/2014 | Metzger et al. | |

FOREIGN PATENT DOCUMENTS

| | | |
|---|---|---|
| GB | 2512609 | 10/2014 |
| WO | 03059203 | 7/2003 |

\* cited by examiner

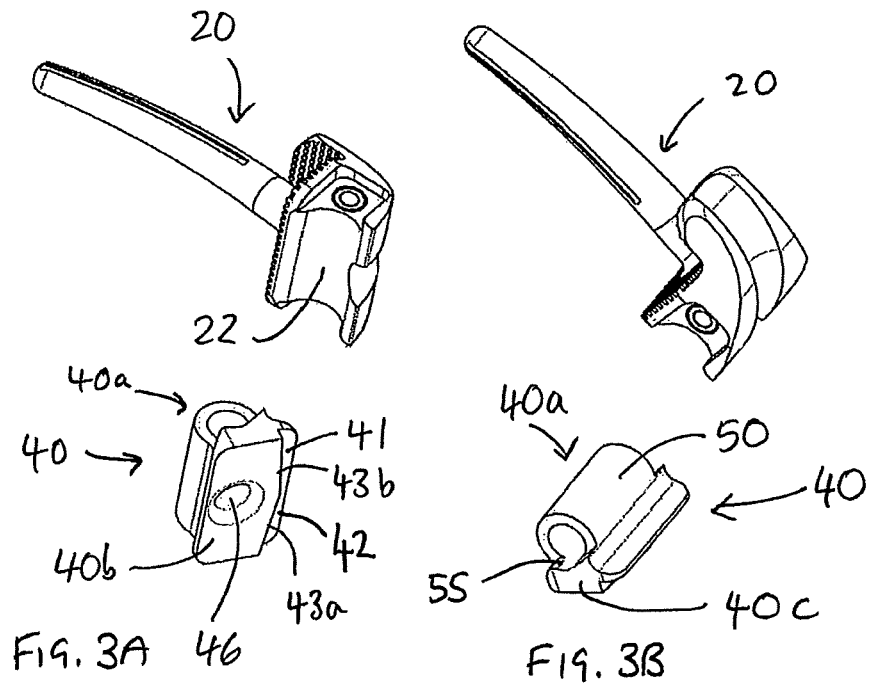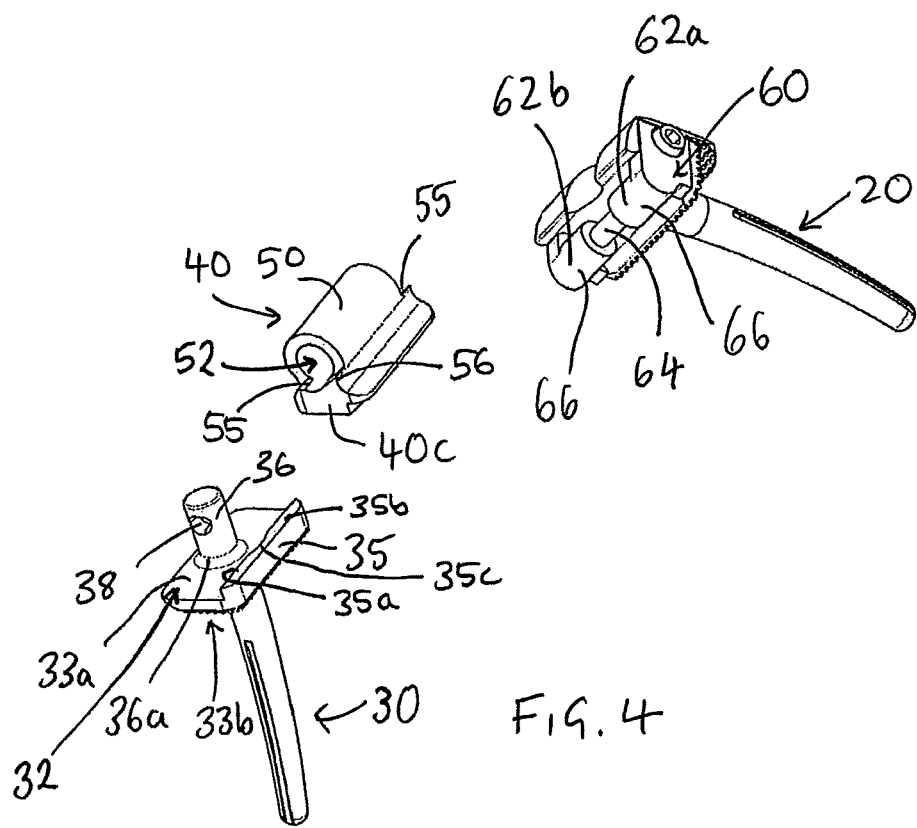

TOTAL KNEE REPLACEMENT PROSTHESIS ASSEMBLY

CROSS REFERENCE TO RELATED APPLICATION

The present application is the U.S. national stage application of International Application PCT/GB2016/052197, filed Jul. 20, 2016, which international application was published on Jan. 26, 2017 as International Publication WO 2017/013428 A1. The International Application claims priority to Great Britain Application 1512696.4, filed Jul. 20, 2015.

FIELD OF THE INVENTION

The invention relates to a total knee replacement (TKR) prosthesis assembly for replacement of a knee joint.

BACKGROUND TO THE INVENTION

The knee joint is made up of the distal end of the femur, which articulates with the proximal end of the tibia, and the patella, which slides in a groove on the femur. Ligaments attach the femur and tibia to provide stability.

The tibiofemoral joint at the knee in humans and animals allows for flexion (bending movement that decreases the angle between the femur and tibia) and extension (straightening movement). In addition to flexion and extension, motion of the knee is both rotational and translational. The femoral condyles both roll and glide as they articulate with respect to the tibial plateaus. The tibiofemoral joint has a 'screw-home' mechanism wherein during knee extension the tibia rotates externally, and this motion is reversed when the knee flexes, providing external and internal rotation within the knee joint.

In humans, knee joint replacements are commonly used for treatment of a variety of clinical conditions and there are a large number of designs to choose from. This is not true for the treatment of canine or feline populations where in the majority of cases euthanasia is usually a solution and for a few where there are a limited number of designs in the market that are available, these all have a very limited application and clinical function. In contrast to human applications the usage and loadings in four legged animals are considerably different, thus requiring a different approach to knee joint replacement.

The rotating hinge knee mechanism is a human knee joint replacement mechanism that was designed to provide a stable total knee reconstruction when the intrinsic stability of the knee has been lost as a result of a severe soft tissue compromise. Prior art rotating hinge knee designs have a transversely oriented hinge axis for flexion-extension motion and a vertically oriented post-in-channel axis for internal and external rotation by means of a post extending down from a bearing component being received in a channel in the tibial component. The post-in-channel design also allows distraction up to the limits imposed by soft-tissue tension. Component dislocation due to distraction is prevented only by the restraint of the soft-tissue envelope and dislocation is a potential problem with this knee replacement design. The amount of distraction required for implant dislocation is related to factors such as the length of the post and degree of taper of the post etc.

The canine and feline knee is anatomically comparable to the human knee. The bone contour, the ligamentous stabilizers (passive restraints) and the muscular support (active restraints) are similar. However, the forces acting on the knee are different for canines and felines due to the normal bent-knee stance of canines and felines, compared to the upright stance in humans.

There is a need for a knee joint replacement prosthesis that is suitable for use in quadrupeds, whose requirements for a knee joint replacement are different from those for bipeds. Features of such a knee joint replacement prosthesis may of course be suitable for knee joint replacement in a biped also.

SUMMARY OF THE INVENTION

According to a first aspect of the invention there is provided a total knee replacement prosthesis assembly comprising a femoral component, a tibial component having a tibial platform, and a bearing component, the bearing component having an inferior side and a superior side, the bearing component being adapted to be arranged between the femoral component and tibial platform when assembled, the tibial platform having a post upstanding from it and the bearing component having a post recess in its inferior side for receiving the post, the bearing component being rotatable about the post when assembled, the post and bearing component each having a transverse bore and the assembly further comprising an axle, at least part of the axle being received through the transverse bore in the post when assembled and at least part of the axle being received through the transverse bore in the bearing component when assembled, the axle being configured to provide an axis of rotation between the femoral component and bearing component which is fixed relative to the femoral component and the bearing component in use. The axle hingedly connects the femoral component and the tibial component and defines a medial-lateral hinge axis, thus preventing the articulation from dislocation and the assembly has a rotating platform provided by the bearing component resting on the tibial platform with a predefined rotational laxity. The medial-lateral hinge axis is rotatable to a limited degree relative to the tibial component about the axis of the post.

Preferably the superior side of the bearing component includes a convex outer bearing surface and the femoral component includes a concave bearing surface for engaging with the convex outer bearing surface of the bearing component in use. Preferably at least part of bearing surface of femoral component is cylindrically curved. In other words the concave bearing surface of the femoral component is preferably a partial cylinder. Preferably at least part of the bearing surface of superior side of the bearing component is cylindrically curved. In other words the outer convex bearing surface of the bearing component is a partial cylinder. The radius of curvature of the concave bearing surface of the femoral component and the convex bearing surface of the superior side of the bearing component preferably substantially match one another. The concave bearing surface of the femoral component is preferably a continuous concave surface, with no sharp angles on the bearing surface. Therefore, the assembly provides a bicondylar replacement implant with a single continuous, unbroken femoral bearing surface. The concave bearing surface of the femoral component is preferably wider than a patellar track on the femoral component. The concave bearing surface of the femoral component is preferably sized to span across the medial and lateral tibio-femoral compartments at the subject's knee.

Preferably the axle includes two axle side portions and an intermediate portion between said axle side portions, the intermediate portion being configured to be received through the transverse bore of the post when assembled, the diameter of the intermediate portion being smaller than that of the axle side portions. Preferably each axle side portion has an outer bearing surface for engaging an inner bearing surface of the bearing component in use. The axle side portions are preferably configured to be situated either side of the post in use. The axle side portions are preferably arranged one at or towards each end of the axle. The axle preferably has a non-uniform diameter along its axis. Similarly, the transverse bore of the bearing component is preferably non-uniform in diameter along its axis for receiving an axle of non-uniform diameter. The transverse bore of the bearing component preferably has two generally hollow cylindrical end portions, one at each end, each for receiving an axle side portion.

Preferably the axle includes first and second axle side members and a pin, each axle side member including an outer bearing surface which is larger in diameter than the pin diameter and each axle side member having a pin receiving recess for receiving part of said pin therein, wherein the axle can be arranged with part of the pin received in the first axle side member, part of the pin received in the second axle side member and an intermediate portion of the pin spanning between the first and second side members, such that said intermediate portion of the pin can be received in the transverse bore of the post when assembled. The axle side members suitably form said axle side portions of the axle and the intermediate portion of the pin suitably forms said intermediate portion of the axle. The axle side members are preferably configured to be situated either side of the post in use. The axle side members each include a female sleeve for receiving part of the pin. The pin is preferably provided initially separate from the axle side members and assembled thereto during installation. Once assembled, the pin is suitably arranged collinearly with the axle side members.

Preferably each axle side member includes an arm which is rigidly coupleable to the femoral component such that the side member can be rigidly coupled relative to the femoral component. Each side axle member may include an integral arm, however the arm may be rigidly coupleable to the side axle member. The femoral component preferably has a recessed area on each of its lateral and medial sides for receiving a corresponding arm for coupling an axle side member thereto. The assembly preferably includes means for rigidly coupling each arm to the femoral component. Said means may be threaded bolts.

Preferably the bearing component has two guide surfaces, one at each end of the transverse bore, each guide surface being configured to engage with an outer surface of one of the axle side members when assembled. When the axle side members are received in the transverse bore of the bearing component, preferably each arm is situated adjacent an end of the transverse bore and a part of the outer surface of each axle side member which extends outside of the transverse bore engages with a corresponding guide surface on the bearing component.

Preferably the bore of the bearing component includes two generally hollow cylindrical end portions, one at each end of the bore. The two generally hollow cylindrical end portions preferably provide inner bearing surfaces of the bearing component. Each end portion of the bore is preferably configured to receive an axle side portion/axle side member of the axle therein. Each end portion of the transverse bore of the bearing component preferably includes an internal cylindrical bearing surface for engaging with an axle side portion/axle side member of the axle in use. The transverse bore of bearing component preferably has a non-uniform diameter along its length. The diameter of the end portions of the transverse bore of the bearing component are preferably each sized such that an axle side portion/axle side member of the axle can be received therein and the diameter of the intermediate section of the transverse bore of the bearing component is preferably sized such that the intermediate portion of the axle can be received therein.

Preferably the bore of the bearing component includes an intermediate portion spanning between the end portions, the diameter of the end portions being larger than the intermediate portion.

Preferably the post recess intersects the intermediate portion of the transverse bore in the bearing component. The post recess is preferably substantially orthogonal to the transverse bore in the bearing component.

Preferably the superior side of the bearing component is convexly curved in the sagittal plane only. In other words, the convex bearing surface of the bearing component is not curved in the coronal plane.

Preferably the femoral component includes a bearing surface which is concavely curved in the sagittal plane only. In other words, the concave bearing surface of the femoral component is not curved in the coronal plane.

Preferably the axle is non-moveable relative to the femoral component in normal use. The axle may be detachable from the femoral component, but once assembled, it does not move relative to the femoral component.

Preferably the axle is coupled rigidly to the femoral component in use. The assembly preferably includes means for rigidly coupling the axle to the femoral component. Said means may be threaded bolts.

Preferably the transverse bore of the post is configured to allow rotation of the axle relative to the post substantially in the transverse plane. Rotation is suitably permitted to a limited degree.

Preferably the transverse bore of the post is flared outwardly at each end to allow rotation of the axle relative to the post substantially in the transverse plane.

Preferably the assembly further comprises a bearing sleeve for receipt within the transverse bore of the post. The bearing sleeve may be received around part of the axle in use. The bearing sleeve is preferably received around the intermediate portion of the pin in use.

Preferably the bearing sleeve is made of a plastic material. Preferably the bearing component is made of a plastic material. The plastic components may be made of any tough, wear-resistant, resilient material such as high density polyethylene. Alternatively, the plastic material may be another suitable polymer material such as Polyether ether ketone (PEEK).

Preferably the femoral component, tibial component and axle are made of a metallic material. The femoral component, tibial component, pin and side components may be independently selected from suitable metals including cobalt-chrome or titanium alloy.

According to a further aspect of the invention there is provided a kit for assembly into a total knee replacement prosthesis assembly according to the invention, wherein the kit comprises the parts of the assembly.

A method for installing a total knee replacement prosthesis assembly according to the present invention is also provided.

According to a further aspect of the invention there is provided a computer-readable medium encoded with instructions for creating a total knee replacement prosthesis assembly according to the invention including instructions for defining the parts of the assembly.

Human anatomical terms such as posterior, anterior, superior, inferior have been used herein, however these are relative terms and it will be understood that these terms can be substituted with the corresponding zootomical terms relevant to the anatomy of a four-legged animal. Anatomical directional terms have been used herein in relation to the parts of the prosthesis assembly. Such terms correspond to the directions relative to a subject when the assembly is implanted in a subject, however it will be understood that these terms are used to provide a frame of reference and apply to the assembly whether it is implanted or is outside of the body of a subject.

BRIEF DESCRIPTION OF THE DRAWINGS

A preferred embodiment of the present invention will now be more particularly described by way of example only with reference to the accompanying drawings, wherein:

FIG. 3A is an inferior exploded perspective view of the femoral component and bearing component;

FIG. 3B is a superior exploded perspective view of the femoral component and bearing component;

FIG. 4 is a perspective view of the femoral component, axle, bearing component and tibial component;

DESCRIPTION OF THE PREFERRED EMBODIMENTS

Figure 1:
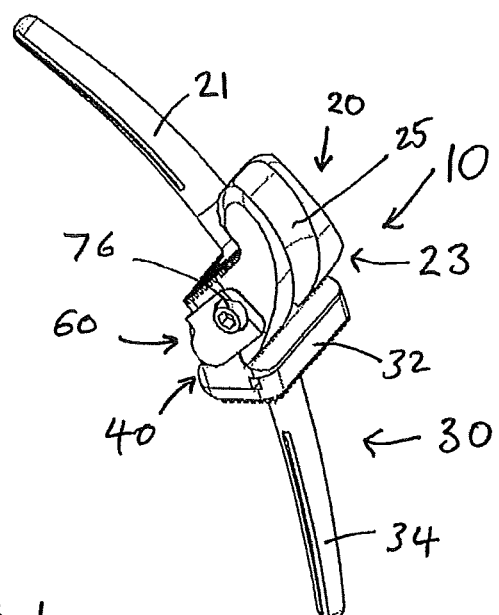
FIG. 1 is a perspective view of an assembled total knee replacement prosthesis (TKR) assembly according to the invention, with the prosthesis shown in the extended configuration.

The present embodiments represent currently the best ways known to the applicant of putting the invention into practice. But they are not the only ways in which this can be achieved. They are illustrated, and they will now be described, by way of example only.

Referring to FIGS. 1 to 6, a total knee replacement prosthesis assembly 10 is shown for replacing a knee joint. The assembly shown in FIGS. 1 to 6 is suitable for replacing a left knee joint in a quadruped, however it will be understood that the features are also suitable for an assembly for implantation in a knee joint in a biped and that the features can be incorporated into a right knee joint replacement assembly.

The assembly 10 includes a femoral component 20, a tibial component 30, a bearing component 40 and an axle 60. The femoral component has a femoral stem 21 adapted to be received by an intramedullary canal of a femur and a distal portion 23 at the distal end of the femoral stem 21, configured to articulate with the bearing component 40. The distal portion 23 of the femoral component 20 has a patellar track 25 for slidingly receiving a prosthetic or natural patella when implanted. The tibial component 30 comprises a tibial platform 32 and a tibial stem 34 adapted to be received by an intramedullary canal of a tibia. The bearing component 40 is adapted to be arranged between the femoral component 20 and the tibial platform 32 when assembled. The bearing component 40 is a mobile bearing component.

Referring to FIG. 4, the tibial platform 32 has a superior surface 33a that faces the bearing component 40 when assembled and an inferior surface 33b for facing the tibia when implanted. The tibial platform 32 has a substantially cylindrical projection or post 36 extending away from the superior surface 33a of the platform. The post 36 extends substantially orthogonally away from the superior surface 33a. The end of the post 36 furthest from the tibial platform 32 is substantially flat in this embodiment, however it may be other than flat, such as dome shaped.

Referring to FIGS. 3A and 3B, the bearing component 40 has a superior side 40a for facing the femoral component when assembled and an inferior side 40b for facing the tibial platform 32 when assembled. The inferior side 40b has a projection recess or post recess 46 for receiving the post 36 of the tibial platform 32. The post recess 46 is shaped to receive the post 36, the post recess 46 being substantially cylindrical in shape and forming a pocket to receive the post. The opening to the post recess 46 is chamfered so as to receive a chamfered part 36a at the base of the post 36. When assembled, the bearing component 40 sits on the tibial platform 32 with the post 36 extending into the post recess 46. The diameter of the post recess 46 is sized to provide a snug fit around the post 36 to provide a fixed axis of rotation for the bearing component 40. This provides for stable rotation of the bearing component 40 relative to the tibial platform 32. Alternatively the diameter of the post recess 46 may be large enough relative to that of the post 36 to allow for some translation of the bearing component 40 relative to the tibial platform 32 when assembled The superior side 40a of the bearing component 40 includes a convex outer bearing surface 50 which engages a concave bearing surface 22 of the femoral component 20 when assembled. The convex outer bearing surface 50 of the bearing component 40 is convexly curved in the sagittal plane and is not curved in the coronal plane, therefore providing a partial cylinder on the superior side 40a of the bearing component 40. The concave bearing surface 22 of the femoral component has a curvature which matches that of the convex outer bearing surface 50 of the bearing component 40. The concave bearing surface 22 of the femoral component has a substantially constant radius of curvature. The convex outer bearing surface 50 of the bearing component 40 also has a substantially constant radius of curvature, which substantially matches that of the femoral component 20.

Figure 6:
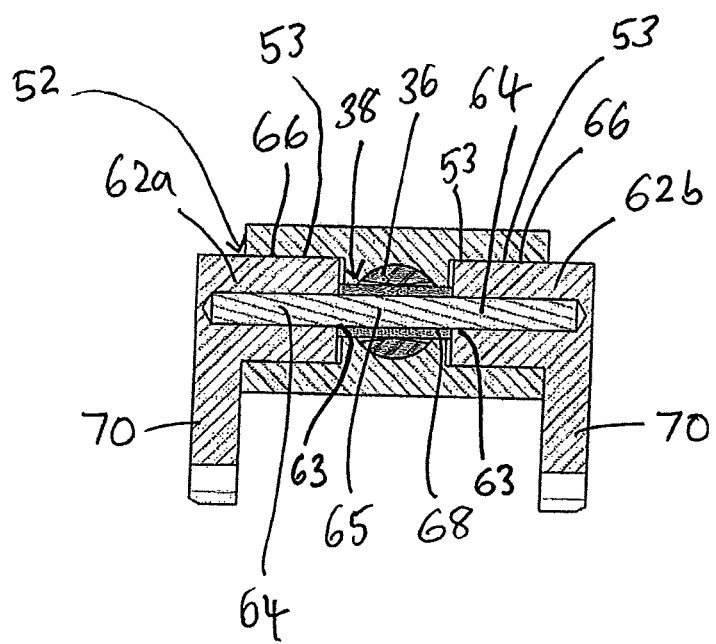
FIG. 6 is a cross-sectional view through the bearing component and axle along plane A-A shown in FIG. 2A.

Referring to FIG. 4 the bearing component 40 has a transverse bore 52 extending between its medial and lateral sides for receiving the axle 60. The post 36 also has a transverse bore 38 extending between its medial and lateral sides for receiving part of the axle 60. The axle comprises first and second axle side members 62a,62b arranged on the lateral and medial side of the axle 60 respectively, and a pin 64 that is received by and spans between the two axle side members 62a,62b. Both axle side members 62a,62b are the same in construction except that they are reversed to assemble to the lateral side and medial side of the joint assembly respectively. Referring to FIG. 6, each axle side member 62a,62b has a pin receiving recess 63 for receiving an end of the pin 64 therein. Each pin receiving recess 63 is a blind bore shaped to form a tight friction fit around the pin 64. When the axle 60 is assembled with the two axle side members 62a,62b assembled on the respective ends of the pin 64 and with the pin receiving recesses 63 facing each other, an intermediate portion 65 of the pin 64 spans between the axle side members 62a,62b. The axle side members 62a,62b each have an outer convex bearing surface 66 which is substantially cylindrical in shape. The outer convex bearing surfaces 66 of the axle side members 62a,62b have a larger diameter than the pin 64, therefore when assembled the axle 60 has a narrow diameter intermediate portion comprising the intermediate portion 65 of the pin which spans between the larger diameter axle side members 62a, 62b on either side. The transverse bore 38 in the post 36 is sized such that the pin 64 can pass therethrough and when assembled the intermediate portion 65 of the pin is situated in the transverse bore 38 in the post 36.

The transverse bore 52 of the bearing component 40 is shaped to receive the outer convex bearing surfaces 66 of the axle side members 62a,62b, the bore 52 having two generally hollow cylindrical portions 53, one at each end of the bore 52. Spanning between the two generally hollow cylindrical portions 53 at each end of the bore 52 is an intermediate portion 54 shaped and sized to receive a bearing sleeve 68 within which is received the pin 64. The post recess 46 intersects the intermediate portion 54 of the transverse bore 52 in the bearing component 40 so that the pin 64, in its bearing sleeve 68, can pass through the bore 52 in the bearing component 40 and bore 38 in the post 36.

Referring to FIG. 6, the transverse bore 38 of the post 36 is flared outwardly at its medial and lateral ends to allow rotation of the axle 60 relative to the post 36 in the transverse plane to at least some degree. This permits some rotation of the axle 60 about the post 36 in the transverse plane.

Figure 5:
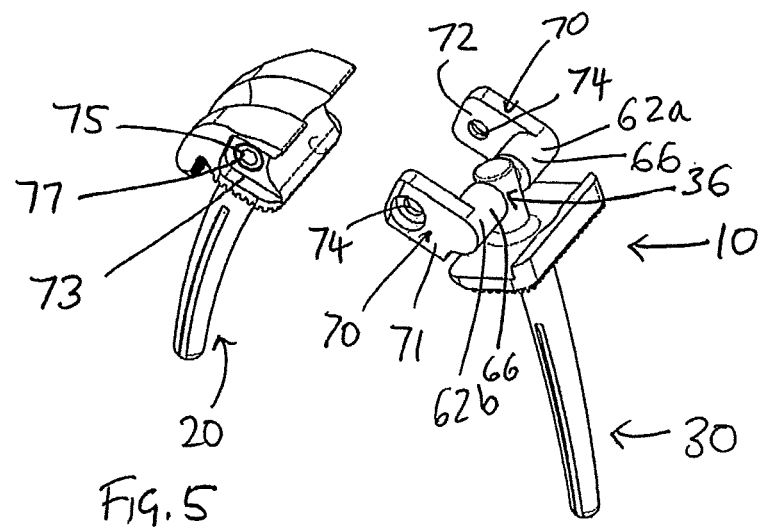
FIG. 5 is an exploded view of the assembly showing the femoral component separate from the other components and without the bearing component.

One of the first and second axle side members 62a,62b will be further described, it being understood that the other contains identical but reversed parts. Referring to FIG. 5, the axle side member 62a/62b has an arm 70 which extends away from the longitudinal axis of the axle 60 and is used to rigidly fix the axle side member 62a/62b to the femoral component 20. The arm 70 has a substantially planar body which lies substantially parallel with the sagittal plane when installed, with an outer surface 71 and a femoral component engaging surface 72. The femoral component 20 has two recessed areas or pockets 73, one on each of the medial and lateral sides of the distal portion 23 of the femoral component 20. Each recessed area 73 is shaped to receive an arm 70 such that the outer surface of the arm 71 is flush with the side of the distal portion 23 when assembled, so as to provide a flush profile to the femoral component 20 when assembled and so as to register the arm 70 in the desired position relative to the femoral component 20. The arm 70 has a throughbore 74 which passes from the outer surface 71 to the femoral component engaging surface 72. The throughbore 74 is arranged to align with a corresponding hole 75 on the side of the distal portion 23 of the femoral component so that a screw or bolt can be received in the throughbore 74 and aligned hole 75 to secure the arm 70 to the femoral component, thus releasably securing the axle 60 to the femoral component 20. Preferably a threaded bolt 76 is used to secure each arm 70 to the femoral component 20. Preferably each hole 75 in the distal portion 23 of the femoral component has a threaded insert 77 received in it, preferably made of titanium, for threadedly securing the bolt 76 to the femoral component 20.

The bearing component 40 has a base portion 40c at its inferior side 40b on which the outer bearing surface 50 is situated. The base portion 40c extends away from the outer bearing surface 50 to the medial and lateral sides to provide first and second curved guide surfaces 55, one on each of the medial and lateral sides of the bearing component 40.

Figures 2A, 2B:
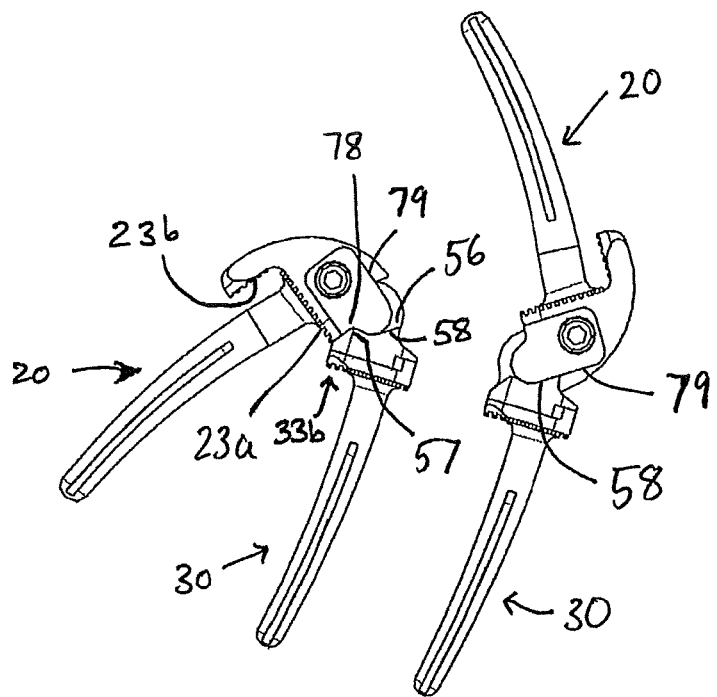
FIG. 2A is a medial side view of the assembly of FIG. 1 with the assembly in the flexed configuration.
FIG. 2B is a medial side view of the assembly of FIG. 1 with the assembly in the extended configuration.

Referring to FIG. 2A, each guide surface 55 slopes from an anterior peak 56, inferiorly, towards the posterior side of the bearing component to provide a planar sloping portion 58, then flattens out before sloping inferiorly and towards the posterior side of the bearing component again, so as to provide a shoulder 57 in the guide surface.

The arm 70 has a proximal end which attaches to the femoral component 20 and a distal end remote from the proximal end. The arm has an anterior side 79 which is straight or includes at least a straight portion. The distal end of the arm 70 is shaped to match the profile of the outer convex bearing surface 66 of the axle side member 62a/62b. When assembled, the distal end of the arm 70 engages the corresponding curved guide surface 55 on the bearing component 40. The distal end of arm 70 also includes a notch 78 which is located and shaped to engage with the corresponding shoulder 57 in the curved guide surface 55. Referring to FIG. 2A, shoulder 57 engages in the corresponding notch 78 on the arm 70 at the predetermined limit of flexion to be accommodated by the joint prosthesis, to prevent hyperflexion of the joint. Referring to FIG. 2B, the anterior side 79 of arm 70 engages the planar sloping portion 58 of the corresponding guide surface 55 at the predetermined limit of extension to be accommodated by the joint prosthesis, to prevent hyperextension of the joint. The joint is configured to allow around 120° of movement between the limit of extension and limit of flexion.

The superior surface 33a of the tibial platform 32 has an abutment 35 extending away from it, to limit the amount by which the bearing component 40 can rotate relative to the tibial component 30 in use which will now be further described. Referring to FIG. 4, the abutment 35 is a straight, elongate, upstanding wall which projects away from the superior surface 33a of the tibial platform 32, the abutment 35 being disposed along the anterior edge of the platform 32, along a medial-lateral axis. The abutment 35 has a posterior face 35a that faces substantially posteriorly and a superior face 35b that faces superiorly when the tibial platform 32 is implanted. The superior face 35b is planar and the posterior face 35a is substantially planar. In the present embodiment, the posterior face 35a of the abutment 35 has a notch 35c at its mid-portion, however this is merely a machining artefact.

Referring to FIG. 3A, the inferior side 40b of the bearing component 40 has an abutment recess 41 for receiving the abutment 35 when assembled. The abutment recess 41 has an inferior face 42, which is planar, for engaging with the superior face 35b of the abutment 35 when assembled. The abutment recess 41 also has first and second faces 43a,43b that face towards the posterior face 35a of the abutment when assembled. The first and second faces 43a,43b are planar and slanted relative to one another. Each of the first and second faces 43a,43b extends from a respective side edge of the bearing component 40 to a common line substantially at a mid-point between the medial and lateral sides of the bearing component 40. The bearing component 40 is rotatable relative to the tibial platform 32 in a plane parallel with the superior surface 33a of the tibial platform 32 to a degree allowed for by the constraints of the first and second faces 43a,43b of the abutment recess 41, which engage with the abutment 35 at the limits of external and internal rotation of the prosthetic knee joint assembly. The post 36 received within the post recess 46 in the bearing component provides an anchor for the bearing component 40, rotation of the axle 60 relative to the post 36 being permitted due to the outward flaring of the ends of the transverse bore 38 in the post 36.

In order to install a TKR assembly of FIGS. 1 to 6, typically the parts of the assembly are assembled during installation. The tibial stem 34 with integral or connected tibial platform 32 will be implanted in the subject's tibia and the femoral stem 21 with integral or connected distal portion 23 will be implanted in the subject's femur. The bearing component 40 is placed on the tibial platform 32 with the post 36 engaged in the post recess 46. An end of the pin 64 is inserted in the pin receiving recess 63 of an axle side member 62 and the bearing sleeve 68 is placed over the intermediate portion 65 of the pin. The pin 64 with bearing sleeve 68 thereon is passed through the transverse bore 52 in the bearing component 40 and through the transverse bore 38 in the post 36 until the axle side member 62 engages in the corresponding hollow cylindrical portion 53 at the end of the bore 52 and the arm 70 of the axle side member 62 is fixed rigidly to the femoral component 20 using a bolt 76. The other side member 62 is inserted in the hollow cylindrical portion 53 at the other end of the bore 52 and its arm 70 is fixed rigidly to the other side of the femoral component 20 using a bolt 76.

In operation, the assembly provides pivoting of the femoral and tibial components relative to one another about the longitudinal axis of the axle and the axle is rotatable to a predefined degree substantially in the transverse plane.

Referring to FIG. 2A, the inferior surface 33b of the tibial platform 32 is stippled to promote attachment to the proximal tibial bone surface. The distal portion 23 of the femoral component 23 has a surface 23a configured to face the distal femoral bone surface when implanted and a surface 23b configured to face the anterior femoral bone surface when implanted, both of which are stippled to promote attachment to bone. The stippled surfaces of the joint assembly are preferably coated with hydroxyapatite (HA) to further promote bone attachment. Treatments other than stippling and/or HA coating can of course be provided on the tibial and femoral components to promote attachment to the bone.

The tibial stem 34 preferably extends from a point on the inferior surface 33b of the tibial platform 32 that is offset medially from a notional mid-point between the medial and lateral sides of the tibial platform. This allows the tibial stem 34 to be optimally located relative to the femoral stem 21 for implantation of the tibial stem 34 in the tibia of a subject. FIGS. 1 to 6 show an assembly for replacement of a left knee joint. The tibial component for replacement of a right knee joint will be a mirror image of the tibial component 30 for a left knee joint in a sagittal mirror plane.

The bearing sleeve 68 and bearing component 40 are preferably made of a tough, wear-resistant, resilient material such as high density polyethylene. Alternatively, they may be made of another suitable polymer material such as polyether ether ketone (PEEK). The tibial component 30, femoral component 20, axle side members 62 and pin 64 are made of a suitable metallic material such as cobalt chrome or titanium alloy. The metallic bearing surfaces may be polished.

The femoral and tibial stems are preferably cemented stems but they may of course be uncemented. The parts of the assembly may be provided in difference sizes to suit different joint sizes.

The present embodiment provides a TKR with a tibial post linked to the femoral component using a transverse pin through the axle acting as a second axle preventing the articulation from dislocation when the knee is flexed and it has a rotating platform provided by the bearing component resting on the tibial platform with a predefined rotational laxity. Additional bearing surface area linked to the femoral component is provided by the two side members or half axles which are received over the ends of the pin. This enhances the durability of the joint.

What is claimed is:

1. A total knee replacement prosthesis assembly comprising
    a femoral component,
    a tibial component having a tibial platform,
    and a bearing component,
    the bearing component having an inferior side and a superior side, the bearing component being adapted to be arranged between the femoral component and tibial platform when assembled, the tibial platform having a post upstanding from it and the bearing component having a post recess in its inferior side for receiving the post, the bearing component being rotatable about the post when assembled,
        the post and bearing component each having a transverse bore and the assembly further comprising an axle, at least part of the axle being received through the transverse bore in the post when assembled and at least part of the axle being received through the transverse bore in the bearing component when assembled, the axle being configured to provide an axis of rotation between the femoral component and bearing component which is fixed relative to the femoral component and the bearing component in use, wherein the superior side of the bearing component includes a convex outer bearing surface and the femoral component includes a concave bearing surface for engaging with the convex outer bearing surface of the bearing component in use.

2. A total knee replacement prosthesis assembly according to claim 1, wherein the axle includes two axle side portions and an intermediate portion between said axle side portions, the intermediate portion being configured to be received through the transverse bore of the post when assembled, the diameter of the intermediate portion being smaller than that of the axle side portions.

3. A total knee replacement prosthesis assembly according to claim 1, wherein the axle includes first and second axle side members and a pin, each axle side member including an outer bearing surface which is larger in diameter than the pin diameter and each axle side member having a pin receiving recess for receiving part of said pin therein, wherein the axle can be arranged with part of the pin received in the first axle side member, part of the pin received in the second axle side member and an intermediate portion of the pin spanning between the first and second axle side members, such that said intermediate portion of the pin can be received in the transverse bore of the post when assembled.

4. A total knee replacement prosthesis assembly according to claim 3, wherein each axle side member includes an arm which is rigidly coupleable to the femoral component such that the axle side member can be rigidly coupled relative to the femoral component.

5. A total knee replacement prosthesis assembly according to claim 4, wherein the bearing component has two guide surfaces, one at each end of the transverse bore, each guide surface being configured to engage with an outer surface of one of the axle side members when assembled.

6. A total knee replacement prosthesis assembly according to claim 1, wherein the transverse bore of the bearing component includes two generally hollow cylindrical end portions, one at each end of the transverse bore of the bearing component.

7. A total knee replacement prosthesis assembly according to claim 6, wherein the transverse bore of the bearing component includes an intermediate portion spanning between the end portions, the diameter of the end portions being larger than the intermediate portion.

8. A total knee replacement prosthesis assembly according to claim 7, wherein the post recess intersects the intermediate portion of the transverse bore in the bearing component.

9. A total knee replacement prosthesis assembly according to claim 1, wherein the superior side of the bearing component is convexly curved in the sagittal plane only.

10. A total knee replacement prosthesis assembly according to claim 1, wherein the femoral component concave bearing surface is concavely curved in the sagittal plane only.

11. A total knee replacement prosthesis assembly according to claim 1, wherein the axle is non-moveable relative to the femoral component.

12. A total knee replacement prosthesis assembly according to claim 1, wherein the axle is coupled rigidly to the femoral component in use.

13. A total knee replacement prosthesis assembly according to claim 1, wherein the transverse bore of the post is configured to allow rotation of the axle relative to the post substantially in the transverse plane.

14. A total knee replacement prosthesis assembly according to claim 13, wherein the transverse bore of the post is flared outwardly at each end to allow rotation of the axle relative to the post substantially in the transverse plane.

15. A total knee replacement prosthesis assembly according to claim 1, wherein the assembly further comprises a bearing sleeve for receipt within the transverse bore of the post.

16. A total knee replacement prosthesis assembly according to claim 15, wherein the bearing sleeve is made of a plastic material.

17. A total knee replacement prosthesis assembly according to claim 1, wherein the bearing component is made of a plastic material.

18. A total knee replacement prosthesis assembly according to claim 1, wherein the femoral component, tibial component and axle are made of a metallic material.

19. A total knee replacement prosthesis assembly comprising a femoral component, a tibial component having a tibial platform, and a bearing component, the bearing component having an inferior side and a superior side, the bearing component being adapted to be arranged between the femoral component and tibial platform when assembled, the tibial platform having a post upstanding from it and the bearing component having a post recess in its inferior side for receiving the post, the bearing component being rotatable about the post when assembled, and the post and bearing component each having a transverse bore and the assembly further comprising an axle, at least part of the axle being received through the transverse bore in the post when assembled and at least part of the axle being received through the transverse bore in the bearing component when assembled, the axle being configured to provide an axis of rotation between the femoral component and bearing component which is fixed relative to the femoral component and the bearing component in use, wherein the axle is non-moveable relative to the femoral component.

* * * * *